United States Patent
Mujawar et al.

(10) Patent No.: US 10,512,501 B2
(45) Date of Patent: Dec. 24, 2019

(54) ELECTROSURGICAL APPARATUS

(71) Applicant: COVIDIEN LP, Mansfield, MA (US)

(72) Inventors: Arifmohamad H. Mujawar, Sangli (IN); Vakula Yenduru, Hyderabad (IN)

(73) Assignee: Covidien LP, Mansfield, MA (US)

( * ) Notice: Subject to any disclaimer, the term of this patent is extended or adjusted under 35 U.S.C. 154(b) by 238 days.

(21) Appl. No.: 15/617,633

(22) Filed: Jun. 8, 2017

(65) Prior Publication Data
US 2018/0353236 A1    Dec. 13, 2018

(51) Int. Cl.
| | | |
|---|---|---|
| A61B 18/00 | (2006.01) | |
| A61B 18/14 | (2006.01) | |
| A61B 17/00 | (2006.01) | |
| A61B 34/30 | (2016.01) | |

(52) U.S. Cl.
CPC .......... *A61B 18/1442* (2013.01); *A61B 34/30* (2016.02); *A61B 2017/00539* (2013.01); *A61B 2018/0063* (2013.01); *A61B 2018/00297* (2013.01); *A61B 2018/00601* (2013.01); *A61B 2018/00773* (2013.01); *A61B 2018/00875* (2013.01);
(Continued)

(58) Field of Classification Search
CPC ........ A61B 18/1442; A61B 2018/1452; A61B 2018/1455; A61B 17/285; A61B 17/295; A61B 2017/00535; A61B 2017/00539
See application file for complete search history.

(56) References Cited

U.S. PATENT DOCUMENTS

| | | |
|---|---|---|
| D249,549 S | 9/1978 | Pike |
| D263,020 S | 2/1982 | Rau, III |
| D295,893 S | 5/1988 | Sharkany et al. |

(Continued)

FOREIGN PATENT DOCUMENTS

| | | |
|---|---|---|
| CN | 201299462 Y | 9/2009 |
| DE | 2415263 A1 | 10/1975 |

(Continued)

OTHER PUBLICATIONS

Heniford et al. "Initial Research and Clinical Results with an Electrothermal Bipolar Vessel Sealer" Oct. 1999.
(Continued)

*Primary Examiner* — Linda C Dvorak
*Assistant Examiner* — James A Cipriano
(74) *Attorney, Agent, or Firm* — Carter, DeLuca & Farrell LLP

(57) ABSTRACT

An electrosurgical forceps includes a first member including a first housing and a first jaw member with a tissue contacting surface. A second member includes a second jaw member with a tissue contacting surface configured to communicate electrosurgical energy with the tissue contacting surface of the first jaw member a fluid receptacle at least partially disposed within the first housing. The fluid receptacle defines first and second receptacle sections, the first receptacle section defining a first internal dimension and the second receptacle section defining a second internal dimension less than the first internal dimension. A fluid is disposed within the fluid receptacle. A trigger plunger is mounted within the fluid receptacle. A knife shaft is at least partially disposed within the fluid receptacle distal of the trigger plunger and the fluid. A knife blade is disposed adjacent the first and second jaw members.

17 Claims, 7 Drawing Sheets

(52) U.S. Cl.
CPC .............. *A61B 2018/00922* (2013.01); *A61B 2018/1455* (2013.01)

(56) References Cited

U.S. PATENT DOCUMENTS

| | | |
|---|---|---|
| D295,894 S | 5/1988 | Sharkany et al. |
| D298,353 S | 11/1988 | Manno |
| D299,413 S | 1/1989 | DeCarolis |
| D343,453 S | 1/1994 | Noda |
| D348,930 S | 7/1994 | Olson |
| D349,341 S | 8/1994 | Lichtman et al. |
| D354,564 S | 1/1995 | Medema |
| D358,887 S | 5/1995 | Feinberg |
| D384,413 S | 9/1997 | Zlock et al. |
| H001745 H | 8/1998 | Paraschac |
| D402,028 S | 12/1998 | Grimm et al. |
| D408,018 S | 4/1999 | McNaughton |
| D416,089 S | 11/1999 | Barton et al. |
| D424,694 S | 5/2000 | Tetzlaff et al. |
| D425,201 S | 5/2000 | Tetzlaff et al. |
| H001904 H | 10/2000 | Yates et al. |
| D449,886 S | 10/2001 | Tetzlaff et al. |
| D453,923 S | 2/2002 | Olson |
| D454,951 S | 3/2002 | Bon |
| D457,958 S | 5/2002 | Dycus et al. |
| D457,959 S | 5/2002 | Tetzlaff et al. |
| H002037 H | 7/2002 | Yates et al. |
| D465,281 S | 11/2002 | Lang |
| D466,209 S | 11/2002 | Bon |
| D493,888 S | 8/2004 | Reschke |
| D496,997 S | 10/2004 | Dycus et al. |
| D499,181 S | 11/2004 | Dycus et al. |
| D502,994 S | 3/2005 | Blake, III |
| D509,297 S | 9/2005 | Wells |
| D525,361 S | 7/2006 | Hushka |
| D531,311 S | 10/2006 | Guerra et al. |
| D533,274 S | 12/2006 | Visconti et al. |
| D533,942 S | 12/2006 | Kerr et al. |
| D535,027 S | 1/2007 | James et al. |
| D538,932 S | 3/2007 | Malik |
| D541,418 S | 4/2007 | Schechter et al. |
| D541,611 S | 5/2007 | Aglassinger |
| D541,938 S | 5/2007 | Kerr et al. |
| D545,432 S | 6/2007 | Watanabe |
| D547,154 S | 7/2007 | Lee |
| D564,662 S | 3/2008 | Moses et al. |
| D567,943 S | 4/2008 | Moses et al. |
| D575,395 S | 8/2008 | Hushka |
| D575,401 S | 8/2008 | Hixson et al. |
| D582,038 S | 12/2008 | Swoyer et al. |
| D617,900 S | 6/2010 | Kingsley et al. |
| D617,901 S | 6/2010 | Unger et al. |
| D617,902 S | 6/2010 | Twomey et al. |
| D617,903 S | 6/2010 | Unger et al. |
| D618,798 S | 6/2010 | Olson et al. |
| D621,503 S | 8/2010 | Otten et al. |
| D627,462 S | 11/2010 | Kingsley |
| D628,289 S | 11/2010 | Romero |
| D628,290 S | 11/2010 | Romero |
| D630,324 S | 1/2011 | Reschke |
| D649,249 S | 11/2011 | Guerra |
| D649,643 S | 11/2011 | Allen, IV et al. |
| D661,394 S | 6/2012 | Romero et al. |
| D670,808 S | 11/2012 | Moua et al. |
| D680,220 S | 4/2013 | Rachlin |
| 8,906,018 B2 * | 12/2014 | Rooks .................... A61B 17/28 606/52 |
| 9,084,608 B2 | 7/2015 | Larson et al. |
| 9,211,657 B2 | 12/2015 | Ackley et al. |
| 2010/0179539 A1 * | 7/2010 | Nau, Jr. ............ A61B 18/1445 606/41 |
| 2013/0150875 A1 * | 6/2013 | McDonell ............ A61F 9/00763 606/170 |
| 2014/0221995 A1 | 8/2014 | Guerra et al. |
| 2014/0221999 A1 | 8/2014 | Cunningham et al. |
| 2014/0228842 A1 | 8/2014 | Dycus et al. |
| 2014/0230243 A1 | 8/2014 | Roy et al. |
| 2014/0236149 A1 | 8/2014 | Kharin et al. |
| 2014/0243811 A1 | 8/2014 | Reschke et al. |
| 2014/0243824 A1 | 8/2014 | Gilbert |
| 2014/0249528 A1 | 9/2014 | Hixson et al. |
| 2014/0250686 A1 | 9/2014 | Hempstead et al. |
| 2014/0257274 A1 | 9/2014 | McCullough, Jr. et al. |
| 2014/0257283 A1 | 9/2014 | Johnson et al. |
| 2014/0257284 A1 | 9/2014 | Artale |
| 2014/0257285 A1 | 9/2014 | Moua |
| 2014/0276803 A1 | 9/2014 | Hart |
| 2014/0284313 A1 | 9/2014 | Allen, IV et al. |
| 2014/0288549 A1 | 9/2014 | McKenna et al. |
| 2014/0288553 A1 | 9/2014 | Johnson et al. |
| 2014/0330308 A1 | 11/2014 | Hart et al. |
| 2014/0336635 A1 * | 11/2014 | Hart .................... A61B 17/2804 606/41 |
| 2014/0353188 A1 | 12/2014 | Reschke et al. |
| 2015/0018816 A1 | 1/2015 | Latimer |
| 2015/0025528 A1 | 1/2015 | Arts |
| 2015/0032106 A1 | 1/2015 | Rachlin |
| 2015/0051598 A1 | 2/2015 | Orszulak et al. |
| 2015/0051640 A1 | 2/2015 | Twomey et al. |
| 2015/0066026 A1 | 3/2015 | Hart et al. |
| 2015/0080880 A1 | 3/2015 | Sartor et al. |
| 2015/0080889 A1 | 3/2015 | Cunningham et al. |
| 2015/0082928 A1 | 3/2015 | Kappus et al. |
| 2015/0088122 A1 | 3/2015 | Jensen |
| 2015/0088126 A1 | 3/2015 | Duffin et al. |
| 2015/0088128 A1 | 3/2015 | Couture |
| 2015/0094714 A1 | 4/2015 | Lee et al. |

FOREIGN PATENT DOCUMENTS

| | | |
|---|---|---|
| DE | 02514501 A1 | 10/1976 |
| DE | 2627679 A1 | 1/1977 |
| DE | 03423356 C2 | 6/1986 |
| DE | 03612646 A1 | 4/1987 |
| DE | 3627221 A1 | 2/1988 |
| DE | 8712328 U1 | 2/1988 |
| DE | 04303882 C2 | 2/1995 |
| DE | 04403252 A1 | 8/1995 |
| DE | 19515914 C1 | 7/1996 |
| DE | 19506363 A1 | 8/1996 |
| DE | 29616210 U1 | 11/1996 |
| DE | 19608716 C1 | 4/1997 |
| DE | 19751106 A1 | 5/1998 |
| DE | 19751108 A1 | 5/1999 |
| DE | 19946527 C1 | 7/2001 |
| DE | 20121161 U1 | 4/2002 |
| DE | 10045375 C2 | 10/2002 |
| DE | 202007009165 U1 | 8/2007 |
| DE | 202007009317 U1 | 8/2007 |
| DE | 202007009318 U1 | 8/2007 |
| DE | 10031773 B4 | 11/2007 |
| DE | 202007016233 U1 | 1/2008 |
| DE | 19738457 B4 | 1/2009 |
| DE | 102004026179 B4 | 1/2009 |
| DE | 102008018406 B3 | 7/2009 |
| EP | 1281878 A1 | 2/2003 |
| EP | 1159926 A3 | 3/2003 |
| JP | 61-501068 | 9/1984 |
| JP | 10-24051 A | 1/1989 |
| JP | 11-47150 A | 6/1989 |
| JP | 6-502328 | 3/1992 |
| JP | 6-5106 | 1/1993 |
| JP | 05-40112 | 2/1993 |
| JP | 0006030945 A | 2/1994 |
| JP | 6-121797 A | 5/1994 |
| JP | 6-285078 A | 10/1994 |
| JP | 6-511401 | 12/1994 |
| JP | 06343644 A | 12/1994 |
| JP | 07265328 A | 10/1995 |
| JP | 8-56955 | 5/1996 |
| JP | 08252263 A | 10/1996 |
| JP | 8-289895 A | 11/1996 |
| JP | 8-317934 A | 12/1996 |
| JP | 8-317936 A | 12/1996 |

(56) References Cited

FOREIGN PATENT DOCUMENTS

| | | |
|---|---|---|
| JP | 9-10223 C | 1/1997 |
| JP | 09000538 A | 1/1997 |
| JP | 9-122138 A | 5/1997 |
| JP | 0010000195 A | 1/1998 |
| JP | 10-155798 A | 6/1998 |
| JP | 11-47149 | 2/1999 |
| JP | 11-070124 A | 3/1999 |
| JP | 11-169381 A | 6/1999 |
| JP | 11-192238 A | 7/1999 |
| JP | 11244298 A | 9/1999 |
| JP | 2000-102545 A | 4/2000 |
| JP | 2000-135222 A | 5/2000 |
| JP | 2000342599 A | 12/2000 |
| JP | 2000350732 A | 12/2000 |
| JP | 2001008944 A | 1/2001 |
| JP | 2001-29355 | 2/2001 |
| JP | 2001029356 A | 2/2001 |
| JP | 2001-03400 | 4/2001 |
| JP | 2001128990 A | 5/2001 |
| JP | 2001-190564 A | 7/2001 |
| JP | 2002-136525 A | 5/2002 |
| JP | 2002-528166 A | 9/2002 |
| JP | 2003-116871 A | 4/2003 |
| JP | 2003-175052 A | 6/2003 |
| JP | 2003245285 A | 9/2003 |
| JP | 2004-528869 A | 9/2004 |
| JP | 2005-152663 A | 6/2005 |
| JP | 2005-253789 A | 9/2005 |
| JP | 2005312807 A | 11/2005 |
| JP | 2006-015078 A | 1/2006 |
| JP | 2006-501939 A | 1/2006 |
| JP | 2006-095316 A | 4/2006 |
| JP | 2008-054926 A | 3/2008 |
| JP | 2011125195 A | 6/2011 |
| SU | 401367 A1 | 11/1974 |
| WO | 0036989 A1 | 6/2000 |
| WO | 0059392 A1 | 10/2000 |
| WO | 0115614 A1 | 3/2001 |
| WO | 0154604 A1 | 8/2001 |
| WO | 02/45589 | 6/2002 |
| WO | 06/021269 A1 | 3/2006 |
| WO | 05110264 A3 | 4/2006 |
| WO | 08/040483 A1 | 4/2008 |
| WO | 2011/018154 A1 | 2/2011 |

OTHER PUBLICATIONS

Michael Choti, "Abdominoperineal Resection with the LigaSure Vessel Sealing System and LigaSure Atlas 20 cm Open Instrument"; Innovations That Work, Jun. 2003.

Chung et al., "Clinical Experience of Sutureless Closed Hemorrhoidectomy with LigaSure" Diseases of the Colon & Rectum vol. 46, No. 1 Jan. 2003.

Tinkcler L.F., "Combined Diathermy and Suction Forceps", Feb. 6, 1967 (Feb. 6, 1967), British Medical Journal Feb. 6, 1976, vol. 1, nr. 5431 p. 361, ISSN: 0007-1447.

Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center,Charlotte,NC; Date: Aug. 2003.

Peterson et al. "Comparison of Healing Process Following Ligation with Sutures and Bipolar Vessel Sealing" Surgical Technology International (2001).

"Electrosurgery: A Historical Overview" Innovations in Electrosurgery; Sales/Product Literature; Dec. 31, 2000. (6 pages).

Johnson et al. "Evaluation of a Bipolar Electrothermal Vessel Sealing Device in Hemorrhoidectomy" Sales/Product Literature; Jan. 2004. (1 page).

E. David Crawford "Evaluation of a New Vessel Sealing Device in Urologic Cancer Surgery" Sales/Product Literature 2000.

Johnson et al. "Evaluation of the LigaSure Vessel Sealing System in Hemorrhoidectormy" American College of Surgeons (ACS) Clinicla Congress Poster (2000).

Muller et al., "Extended Left Hemicolectomy Using the LigaSure Vessel Sealing System" Innovations That Work, Sep. 1999.

Kennedy et al. "High-burst-strength, feedback-controlled bipolar vessel sealing" Surgical Endoscopy (1998) 12: 876-878.

Burdette et al. "In Vivo Probe Measurement Technique for Determining Dielectric Properties at VHF Through Microwave Frequencies", IEEE Transactions on Microwave Theory and Techniques, vol. MTT-28, No. 4, Apr. 1980 pp. 414-427.

Carus et al., "Initial Experience With the LigaSure Vessel Sealing System in Abdominal Surgery" Innovations That Work, Jun. 2002.

Heniford et al. "Initial Results with an Electrothermal Bipolar Vessel Sealer" Surgical Endoscopy (2000) 15:799-801. (4 pages).

Herman et al., "Laparoscopic Intestinal Resection With the LigaSure Vessel Sealing System: A Case Report"; Innovations That Work, Feb. 2002.

Koyle et al., "Laparoscopic Palomo Varicocele Ligation in Children and Adolescents" Pediatric Endosurgery & Innovative Techniques, vol. 6, No. 1, 2002.

W. Scott Helton, "LigaSure Vessel Sealing System: Revolutionary Hemostasis Product for General Surgery"; Sales/Product Literature 1999.

LigaSure Vessel Sealing System, the Seal of Confidence in General, Gynecologic, Urologic, and Laparaoscopic Surgery; Sales/Product Literature; Apr. 2002.

Joseph Ortenberg "LigaSure System Used in Laparoscopic 1st and 2nd Stage Orchiopexy" Innovations That Work, Nov. 2002.

Sigel et al. "The Mechanism of Blood Vessel Closure by High Frequency Electrocoagulation" Surgery Gynecology & Obstetrics, Oct. 1965 pp. 823-831.

Sampayan et al, "Multilayer Ultra-High Gradient Insulator Technology" Discharges and Electrical Insulation in Vacuum, 1998. Netherlands Aug. 17-21, 1998; vol. 2, pp. 740-743.

Paul G. Horgan, "A Novel Technique for Parenchymal Division During Hepatectomy" The American Journal of Surgery, vol. 181, No. 3, Apr. 2001 pp. 236-237.

Benaron et al., "Optical Time-of-Flight and Absorbance Imaging of Biologic Media", Science, American Association for the Advancement of Science, Washington, DC, vol. 259, Mar. 5, 1993, pp. 1463-1466.

Olsson et al. "Radical Cystectomy in Females" Current Surgical Techniques in Urology, vol. 14, Issue 3, 2001.

Palazzo et al. "Randomized clinical trial of Ligasure versus open haemorrhoidectomy" British Journal of Surgery 2002, 89, 154-157.

Levy et al. "Randomized Trial of Suture Versus Electrosurgical Bipolar Vessel Sealing in Vaginal Hysterectomy" Obstetrics & Gynecology, vol. 102, No. 1, Jul. 2003.

"Reducing Needlestick Injuries in the Operating Room" Sales/Product Literature 2001. (1 page).

Bergdahl et al. "Studies on Coagulation and the Development of an Automatic Computerized Bipolar Coagulator" J. Neurosurg, vol. 75, Jul. 1991, pp. 148-151.

Strasberg et al. "A Phase I Study of the LigaSure Vessel Sealing System in Hepatic Surgery" Section of HPB Surger, Washington University School of Medicine, St. Louis MO, Presented at AHPBA, Feb. 2001.

Sayfan et al. "Sutureless Closed Hemorrhoidectomy: A New Technique" Annals of Surgery vol. 234 No. 1 Jul. 2001; pp. 21-24.

Levy et al., "Update on Hysterectomy—New Technologies and Techniques" OBG Management, Feb. 2003. (15 pages).

Dulemba et al. "Use of a Bipolar Electrothermal Vessel Sealer in Laparoscopically Assisted Vaginal Hysterectomy" Sales/Product Literature; Jan. 2004.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Sengupta et al., "Use of a Computer-Controlled Bipolar Diathermy System in Radical Prostatectomies and Other Open Urological Surgery" ANZ Journal of Surgery (2001) 71.9 pp. 538-540.

(56) References Cited

OTHER PUBLICATIONS

Rothenberg et al. "Use of the LigaSure Vessel Sealing System in Minimally Invasive Surgery in Children" Int'l Pediatric Endosurgery Group (IPEG) 2000.
Crawford et al. "Use of the LigaSure Vessel Sealing System in Urologic Cancer Surgery" Grand Rounds in Urology 1999 vol. 1 Issue 4 pp. 10-17.
Craig Johnson, "Use of the LigaSure Vessel Sealing System in Bloodless Hemorrhoidectomy" Innovations That Work, Mar. 2000.
Levy et al. "Use of a New Energy-based Vessel Ligation Device During Vaginal Hysterectomy" Int'l Federation of Gynecology and Obstetrics (FIGO) World Congress 1999.
Barbara Levy, "Use of a New Vessel Ligation Device During Vaginal Hysterectomy" FIGO 2000, Washington, D.C.. (1 page).
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
Crouch et al. "A Velocity-Dependent Model for Needle Insertion in Soft Tissue" MICCAI 2005; LNCS 3750 pp. 624-632 Dated: 2005.
McLellan et al. "Vessel Sealing for Hemostasis During Pelvic Surgery" Int'l Federation of Gynecology and Obstetrics FIGO World Congress 2000, Washington, D.C.
McLellan et al. "Vessel Sealing for Hemostasis During Gynecologic Surgery" Sales/Product Literature 1999.
U.S. Appl. No. 08/926,869; filed Sep. 10, 1997; inventor: James G. Chandler, Abandoned.
U.S. Appl. No. 09/177,950; filed Oct. 23, 1998; inventor: Randel A. Frazier, abandoned.
U.S. Appl. No. 09/387,883; filed Sep. 1, 1999; inventor: Dale F. Schmaltz, abandoned.
U.S. Appl. No. 09/591,328; filed Jun. 9, 2000; inventor: Thomas P. Ryan, abandoned.
U.S. Appl. No. 12/336,970; filed Dec. 17, 2008; inventor: Paul R. Sremeich, abandoned.
U.S. Appl. No. 14/065,644; filed Oct. 29, 2013; inventor: Reschke, abandoned.

\* cited by examiner

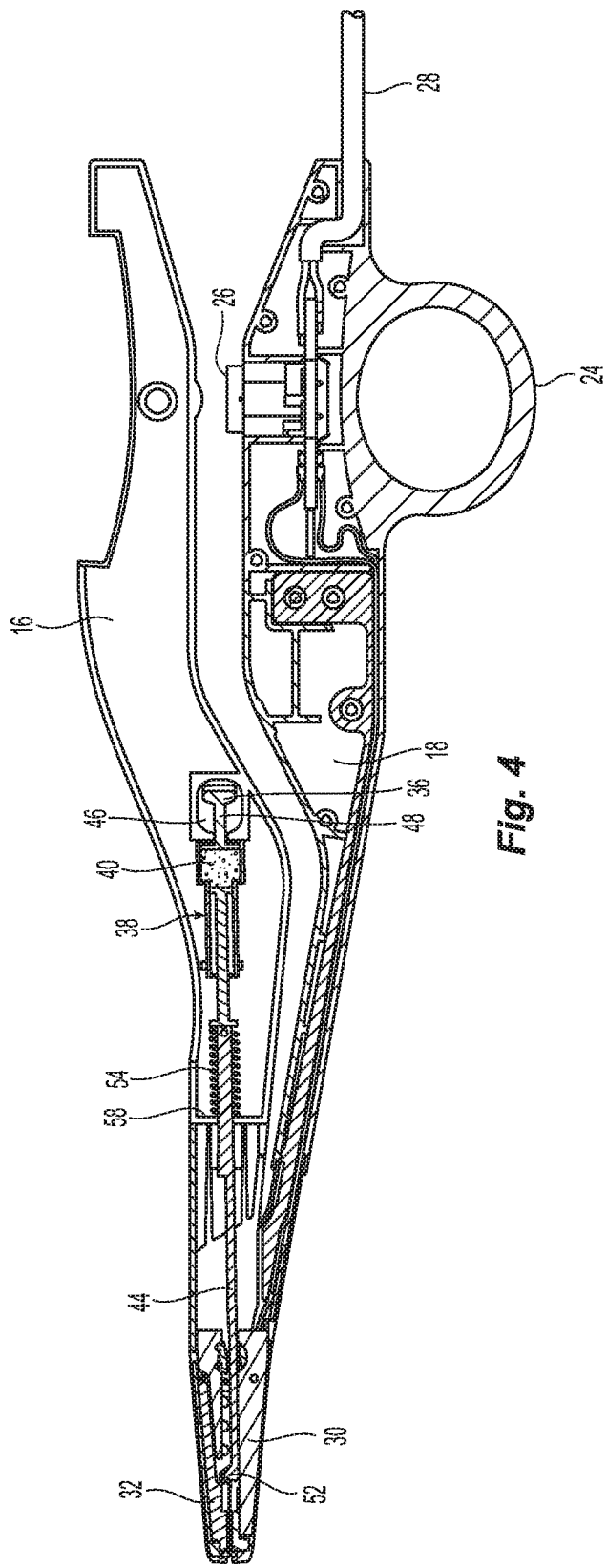
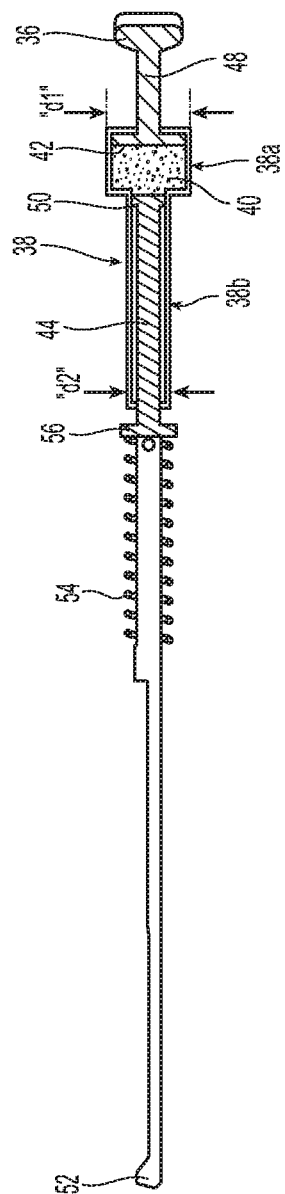
Fig. 4
Fig. 5

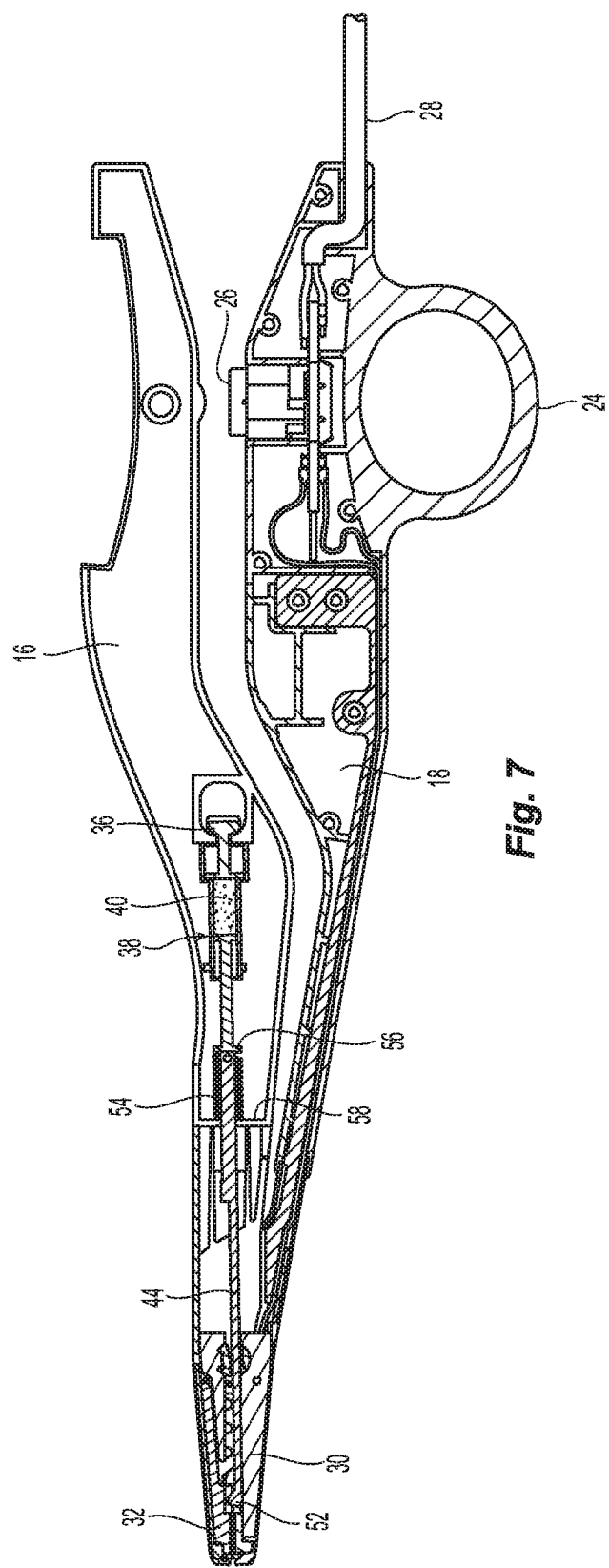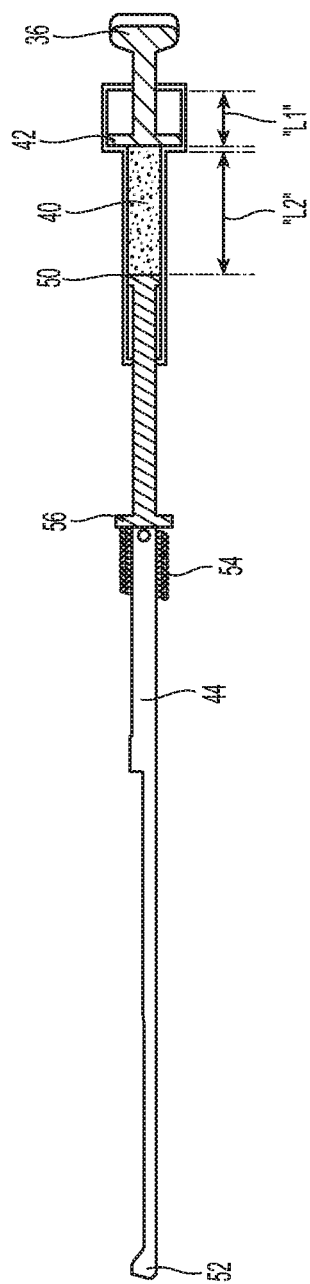

ELECTROSURGICAL APPARATUS

BACKGROUND

1. Technical Field

The present disclosure relates to an electrosurgical apparatus and, more particularly, relates to energy-based surgical forceps for treating, sealing and/or cutting tissue.

2. Background of Related Art

An electrosurgical apparatus applies high frequency electric current to cut, coagulate and/or cauterize tissue. A conventional electrosurgical apparatus is an electrosurgical forceps which is a plier-like instrument relying on mechanical action between its jaws to grasp, clamp, and constrict tissue. The jaws are adapted for relative movement, e.g., between open and approximated conditions. A knife is typically incorporated within the forceps to sever the treated tissue. However, known knife deployment mechanisms are complex in design often requiring multiple linkage mechanisms to obtain the desired travel of the knife relative to the jaws. This increases the overall size of the handle and the range of movement required by the clinician to manipulate an actuator to activate a firing stroke of the knife deployment mechanism.

SUMMARY

Accordingly, the present disclosure is directed to an electrosurgical forceps incorporating a hydraulic knife mechanism adapted to increase linear movement of the cutting blade while minimizing movement of the manually manipulative actuator or trigger. These associated features facilitate actuation of the cutting blade and reduce the collective size of the handle and its trigger components.

In accordance with one embodiment, an electrosurgical forceps includes a first member having a first housing and a first shaft member depending from the first housing where the first shaft member has a first jaw member and a tissue contacting surface, and a second member having a second housing and a second shaft member depending from the second housing where the second shaft member has a second jaw member and a tissue contacting surface configured to communicate electrosurgical energy with the tissue contacting surface of the first jaw member. The second member is configured for movement relative to the first member to cause movement of the first and second jaw members between open and closed positions. A fluid receptacle is at least partially disposed within the first housing, and defines first and second receptacle sections. The first receptacle section has a first internal dimension and the second receptacle section has a second internal dimension less than the first internal dimension. A fluid, e.g., an incompressible fluid, is disposed within the fluid receptacle. A trigger plunger is mounted within the fluid receptacle. A knife shaft is at least partially disposed within the fluid receptacle distal of the trigger plunger and the fluid, and has a knife blade disposed adjacent the first and second jaw members. A manually engageable trigger is mounted to the first housing and coupled to the trigger plunger. The trigger is configured for linear movement a first linear distance to cause the trigger plunger to displace the fluid from the first receptacle section to the second receptacle section to cause corresponding linear movement of the knife shaft a second linear distance greater than the first linear distance whereby the knife blade at least partially traverses the first and second jaw members to sever tissue disposed therebetween.

In embodiments, the knife shaft is configured to move from a retracted position to an extended position upon movement of the trigger the first linear distance. In some embodiments, the knife shaft includes a shaft plunger disposed within the second receptacle section of the fluid receptacle. The shaft plunger is configured to be displaced by the fluid during movement of the trigger through the first linear distance to move the knife shaft to the extended position. In certain embodiments, the knife shaft is normally biased toward the retracted position whereby upon release of the trigger subsequent to movement through the first linear distance, the knife shaft returns toward the retracted position with the shaft plunger displacing the fluid from the second receptacle section to the first receptacle section to cause the trigger plunger and the trigger to return to an initial position.

In embodiments, the fluid receptacle is a step design where the first receptacle section defines a first inner diameter and the second receptacle section defines a second inner diameter. In some embodiments, the ratio of the first inner diameter to the second inner diameter is greater than 1.5:1. In certain embodiments, the ratio of the first inner diameter to the second inner diameter is at least 2:1.

In another embodiment, a surgical forceps includes a first member having a first housing and a first shaft member depending from the first housing where the first shaft member has a first jaw member, and a second member having a second housing and a second shaft member depending from the second housing where the second shaft member has a second jaw member. The second member is configured for movement relative to the first member to cause movement of the first and second jaw members between open and closed positions. A fluid receptacle is at least partially disposed within the first housing, and defines first and second receptacle sections. The first receptacle section has a first internal dimension and the second receptacle section has a second internal dimension less the first internal dimension. A trigger plunger is mounted within the first receptacle section of the fluid receptacle. A knife shaft is at least partially disposed within the second receptacle section, and includes a shaft plunger and a knife blade. An incompressible fluid is disposed within the fluid receptacle between the trigger plunger and the shaft plunger. A manually engageable trigger is mounted to the first housing and coupled to the trigger plunger. The trigger is configured for linear movement through a first linear distance from an initial position to an actuated position to cause the trigger plunger to displace the incompressible fluid from the first receptacle section to the second receptacle section to cause corresponding engagement with the shaft plunger and linear movement of the knife shaft a second linear distance greater than the first linear distance whereby the knife blade at least partially traverses the first and second jaw members to sever tissue disposed therebetween In embodiments, the knife shaft is normally biased to a retracted position whereby, upon release of the trigger subsequent to movement to the actuated position, the shaft plunger engages the incompressible fluid to displace the incompressible fluid from the second receptacle section to the first receptacle section to cause linear movement of the plunger and return of the trigger to the initial position. In some embodiments, a spring is mounted to the first housing and engageable with the knife shaft to normally bias the knife shaft toward the retracted position.

In certain embodiments, the fluid receptacle is a step design where the first receptacle section defines a first inner diameter and the second receptacle section defines a second inner diameter. In embodiments, the ratio of the first inner diameter to the second inner diameter is greater than 1.5:1. In some embodiments, the ratio of the first inner diameter to the second inner diameter is at least 2:1.

In certain embodiments, the first and second jaw members each include tissue contacting surfaces whereby the tissue contacting surfaces are configured to communicate electrical energy therebetween. In some embodiments, an electrosurgical generator is in electrical communication with at least one of the first and second jaw members.

The hydraulic knife mechanism of the electrosurgical forceps increases the distance of movement of the cutting blade while reducing movement required by the trigger. This simplifies the structure of the handle and its operation, and advantageously reduces operator strain and fatigue.

Other features of the present disclosure will be appreciated from the following description.

BRIEF DESCRIPTION OF THE DRAWINGS

Various aspects and features of the present disclosure are described hereinbelow with reference to the drawings wherein like numerals designate identical or corresponding elements in each of the several views:

FIG. 4 is a side cross-sectional view of the electrosurgical forceps illustrating the positioning of the components of the hydraulic knife mechanism prior to actuation of the trigger;

FIG. 5 is an enlarged view illustrating the trigger, the fluid receptacle, the trigger plunger and the knife shaft of the hydraulic knife mechanism prior to actuation of the trigger;

FIG. 7 is a side cross-sectional view similar to the view of FIG. 4 illustrating positioning of the components of the hydraulic knife mechanism subsequent to actuation of the trigger;

FIG. 8 is an enlarged view similar to the view of FIG. 5 illustrating the trigger, the fluid receptacle, the trigger plunger and the knife shaft of the hydraulic knife mechanism subsequent to actuation of the trigger.

DETAILED DESCRIPTION

In this disclosure, the term "proximal" refers to a portion of a structure closer to an operator, while the term "distal" refers to a portion of the same structure further from the clinician. As used herein, the term "subject" refers to a human patient or animal. The term "clinician" refers to a doctor (e.g., a surgeon), a nurse, and other clinicians or care providers, and may include support personnel.

Figure 1:
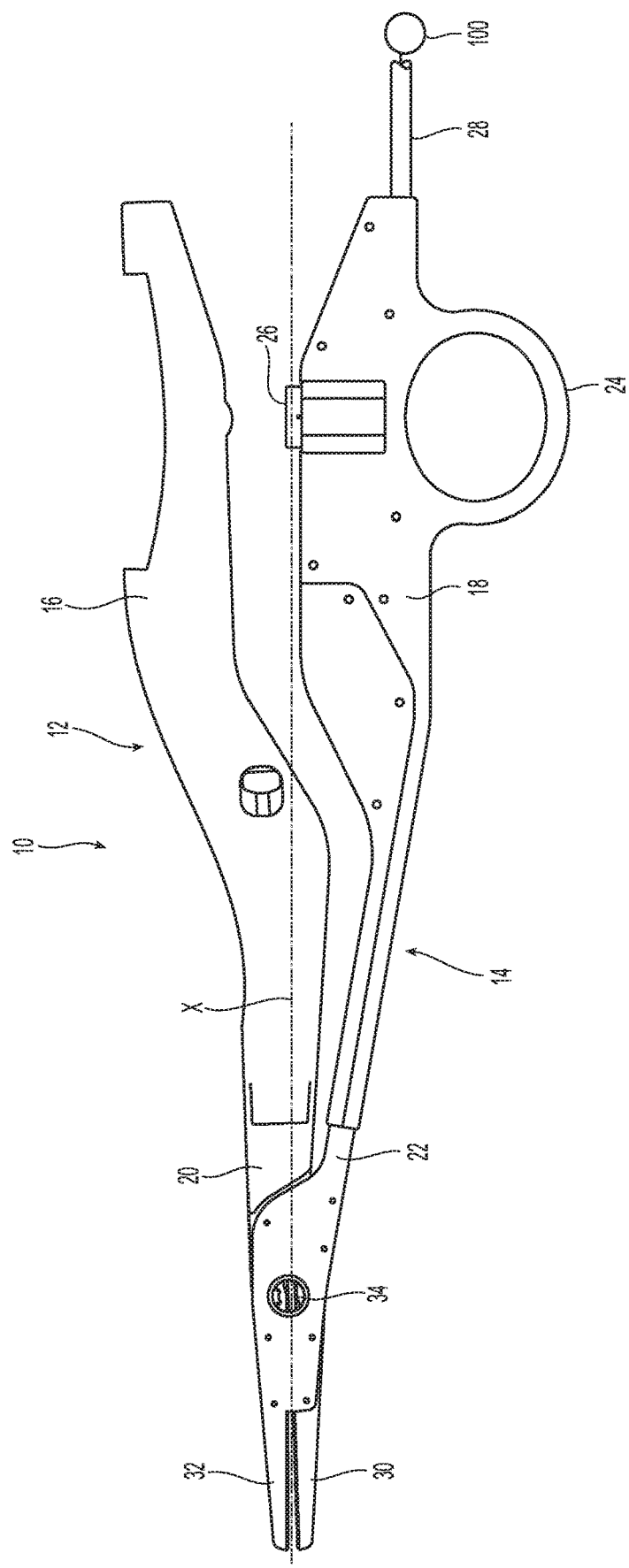
FIG. 1 is a side elevation view of the electrosurgical forceps in accordance with the present disclosure illustrating the first and second housings, first and second shafts and the first and second jaw members with the first and second jaw members in a closed position.
Figure 2:
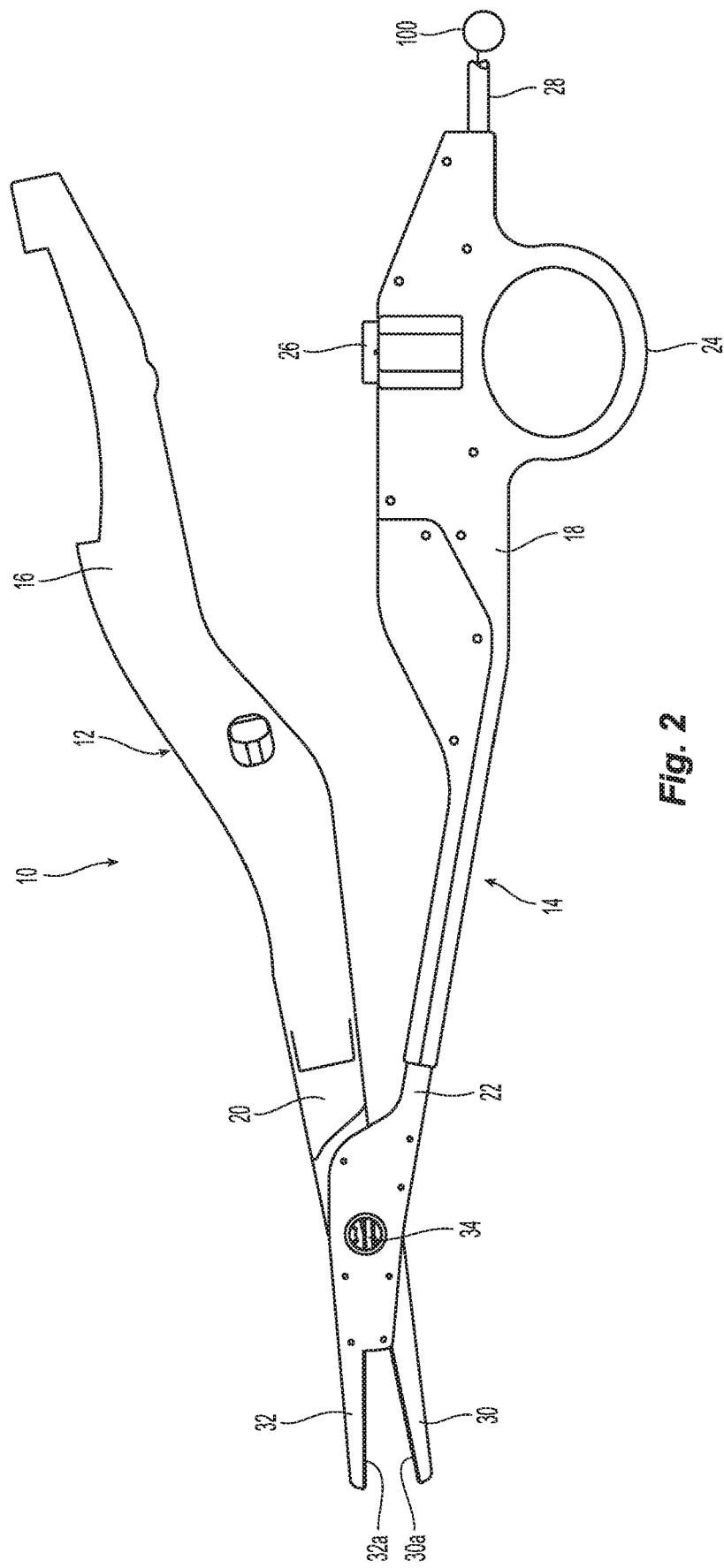
FIG. 2 is a view similar to the view of FIG. 1 illustrating the first and second jaw members in an open position.

Referring initially to FIGS. 1-2, the electrosurgical forceps 10 of the present disclosure is illustrated. The electrosurgical forceps 10 includes a first member 12 and a second member 14 operatively coupled to each other and extending generally along a longitudinal axis "x". The first and second members 12, 14 include respective first and second housings 16, 18 having first and second shafts 20, 22 depending from the first and second housings 16, 18. The first and second housings 16, 18 are configured for manual engagement by the clinician, i.e., form the handle of the electrosurgical forceps, and may be a pliers-like grip. The second housing 18 may have a finger loop 24 for receiving a finger of the clinician. The second housing 18 may include an electrical contact or switch 26 in opposition to the first housing 16 for selectively supplying electrosurgical energy when the first and second housings 16, 18 are approximated. An electrosurgical cable 28 extends from the second housing 18 and is connected to an energy source, e.g., an electrosurgical generator 100.

With continued reference to FIGS. 1-2, a first jaw member 30 is coupled to the first shaft 20 and a second jaw member 32 is coupled to second shaft 22. The first and second jaw members 30, 32 form the end effector of the electrosurgical forceps, which clamps, delivers electro-surgical energy from the energy source 100, and severs tissue. The first and second jaw members 30, 32 have tissue contacting surfaces 30a, 32a, which communicate electrosurgical energy therebetween. In embodiments, the first and second jaw members 30, 32 are integrally formed with the respective first and second shafts 20, 22. The first and second jaw members 30, 32 pivot about a pivot pin 34 between the closed position depicted in FIG. 1 and the open position depicted in FIG. 2. Further details of various operating components of the electrosurgical forceps 10 may be ascertained by reference to commonly assigned U.S. Patent Publication No. 2014/0276803 to Hart, the entire contents of which are hereby incorporated by reference herein.

Figure 3:
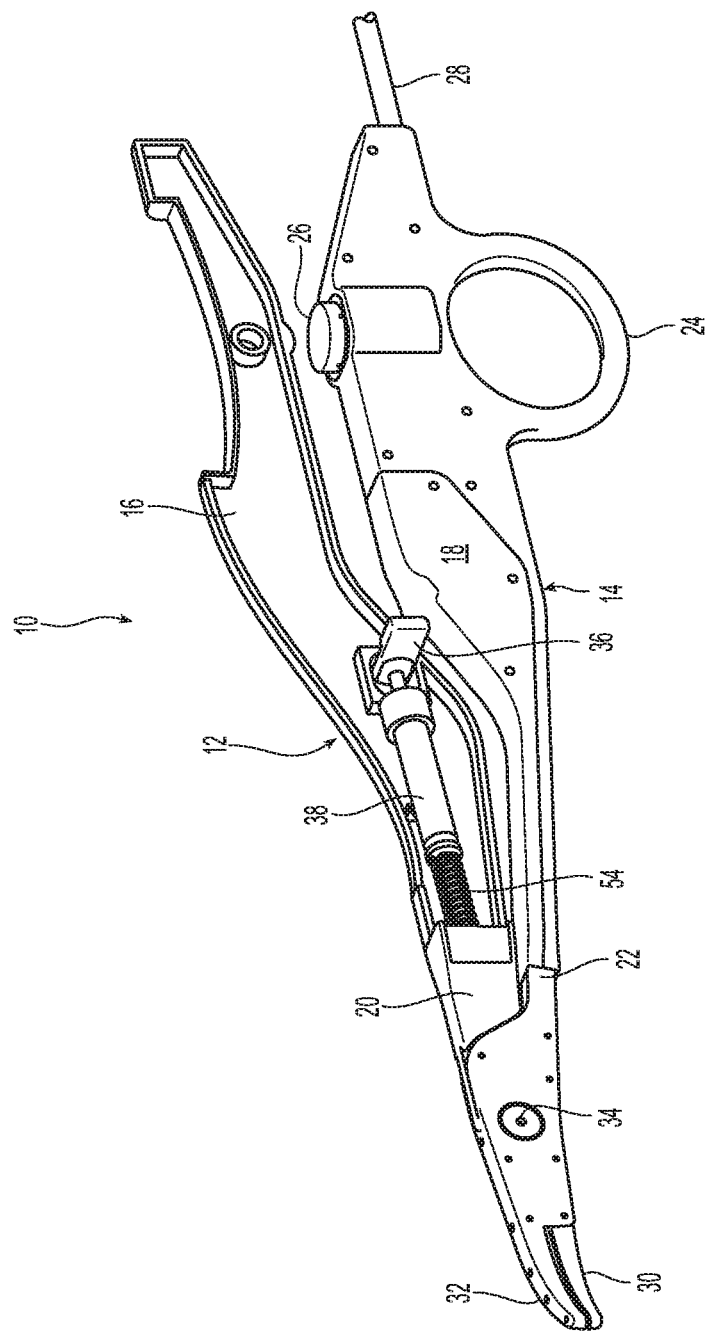
FIG. 3 is a perspective view of the electrosurgical forceps with portions removed illustrating components of the hydraulic knife mechanism.

Referring now to FIGS. 3-5, the hydraulic knife mechanism of the electrosurgical apparatus will be discussed. In FIG. 3, a portion of the first housing 16 is removed to illustrate components of the hydraulic knife mechanism. The hydraulic knife mechanism includes a manually engageable trigger 36, a fluid receptacle 38 containing fluid 40, a trigger plunger 42 disposed within the fluid receptacle 38 and coupled to the trigger 36, and a knife shaft 44 at least partially disposed within the fluid receptacle 38 distal of the fluid 40 and the trigger plunger 42. The manually engageable trigger 36 is mounted within a channel 46 (FIG. 4) formed in the first housing 16 and is adapted for linear movement with respect to the longitudinal axis "x" between initial and actuated positions. In particular, the manually engageable trigger 36 traverses the channel 46 in a distal or advancing direction from the initial position during a firing stroke of the hydraulic knife mechanism and traverses the channel in a retracting or proximal direction from the actuated position toward the initial position during a return stroke of the hydraulic knife mechanism. The trigger plunger 42 is coupled to the trigger 36 through a plunger shaft 48. The trigger plunger 42 may include an elastomeric material to establish a seal (e.g., a sliding seal) within the fluid receptacle 38. In embodiments, the trigger plunger 42 is generally disc-shaped although other configurations are envisioned. The knife shaft 44 includes a shaft plunger 50 (FIG. 5) which is disposed within the fluid receptacle 38. The shaft plunger 50 may also include an elastomeric material to establish a seal (e.g., a sliding seal) within the fluid receptacle 38. The shaft plunger 50 also may be disc-shaped. The knife shaft 44 extends through the first member and terminates in a knife blade 52.

As best depicted in FIG. 5, the fluid receptacle 38 defines first and second receptacle sections 38a, 38b. The first receptacle section 38a is proximal of the second receptacle section 38b and houses the trigger plunger 42. The second receptacle section 38b at least partially accommodates the knife shaft 44. The first receptacle section 38a defines an internal dimension, "d1", e.g., inner diameter, which is greater than the internal dimension, "d2" e.g., inner diameter, of the second receptacle section 38b. In embodiments, the ratio of the first internal dimension "d1" or diameter to the second internal dimension "d2" or diameter is greater than 1.5:1, and may be at least 2:1. For example, the first internal diameter of the first receptacle section may be about 8-10 millimeters (mm) and the second internal diameter of the second receptacle section may be about 5 mm. Other diameters are also envisioned.

The trigger plunger 42 defines a cross-sectional dimension approximating, or substantially equal to, the internal dimension "d1" or diameter of the first receptacle section 38a to establish a seal whereby advancing movement of the trigger plunger 42 through manipulation of the trigger 36 from the initial position to the actuated position during a firing stroke of the hydraulic knife mechanism will force the fluid distally into the second receptacle section 38b. Similarly, the shaft plunger 50 defines a cross-sectional dimension approximating, or substantially equal to, the internal dimension "d2" or diameter of the second receptacle section 38b to establish a seal such that the fluid dispensed from the first receptacle section 38a into the second receptacle section 38b will engage the shaft plunger 50 and drive the shaft plunger 50 and, consequently, the knife shaft 44 in the distal direction. In a similar manner, movement of the hydraulic knife mechanism during a return stroke will cause the shaft plunger 50 to drive the fluid from within the second receptacle section 38b and against the trigger plunger 42 to move the trigger plunger 42 and the trigger 36 in a proximal direction to the initial position of the trigger depicted in FIG. 5.

Referring to FIGS. 3-5, the first housing 16 includes a spring 54, e.g., a coil spring, coaxially mounted about the knife shaft 44. The coil spring 54 engages, at one end, a shelf 56 on the knife shaft 44 and, at its other end, an internal abutment shoulder 58 within the first housing 16. The spring 54 normally biases the knife shaft 44 and the knife blade 52 in the proximal direction corresponding to the retracted position of the knife shaft 44 and the knife blade 52.

The fluid 40 within the fluid receptacle 38 may be in gas or liquid form. In embodiments, the fluid is an incompressible fluid including water, oil or the like.

Figure 6:
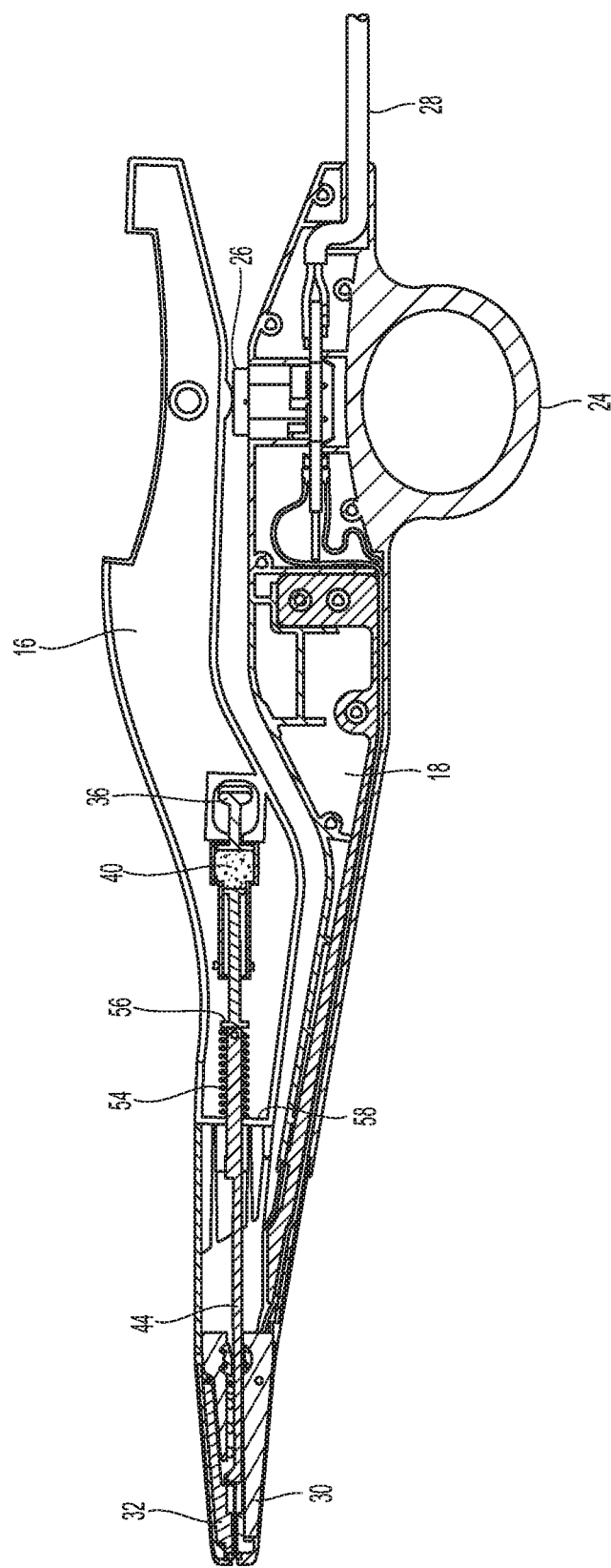
FIG. 6 is a side cross-sectional view of the electrosurgical forceps similar to the view of FIG. 4 illustrating the first housing contacting the contact switch to deliver electrosurgical energy to the first and second jaw members.

The use of the hydraulic knife mechanism with the electrosurgical forceps 10 will now be discussed. A vessel to be treated, e.g., sealed, is identified. The first and second jaw members 30, 32 are moved to the open position of FIG. 2, and positioned about the vessel (not shown). The first and second jaw members 30, 32 are then moved to the closed position of FIG. 1 engaging and compressing the vessel. When it is desired to deliver electrosurgical energy between the first and second jaw members 30, 32, the first housing 16 (which has a degree of flexibility) is flexed downwardly to cause contact and actuation of the switch 26 (FIG. 6) such that electrosurgical energy is delivered from the energy source 100 to the tissue contacting surfaces 30a, 32a of the first and second jaw members 30, 32. Once the vessel is sealed, the first housing 16 is released and displaced from the switch 26 thereby deactivating the switch 26.

With reference to FIGS. 7-8, the manually engageable trigger 36 is manipulated to move a first linear distance within the channel 46 from the initial position to the actuated position. During movement of the trigger 36, the trigger plunger 42 forces the fluid 40 from the first receptacle section 38a to the second receptacle section 38b and drives the fluid 40 against the shaft plunger 50. In turn, the shaft plunger 50, the knife shaft 44 and the knife blade 52 are driven in the distal direction to an extended position such that the knife blade 52 moves within the first and second jaw members 30, 32 and severs the sealed vessel. During this movement, the coil spring 54 is compressed. As best depicted in FIG. 8, the change in the internal dimension between the first receptacle section 38a and the second receptacle section 38b will increase the distance of travel of the knife shaft 44 and the knife blade 52. In particular, the resulting change in the flow dynamics of the fluid 40 between the different-sized first and second receptacle sections 38a, 38b will move the knife shaft 44 and the knife blade 52 a second linear distance substantially greater than the first linear distance of the trigger 36 and the trigger plunger 42. As one example, in an embodiment where the internal dimension or diameter of the first receptacle section 38a is twice the internal dimension or diameter of the second receptacle section 38b, the second distance will increase by a factor of four, i.e., 400%.

Figure 9:
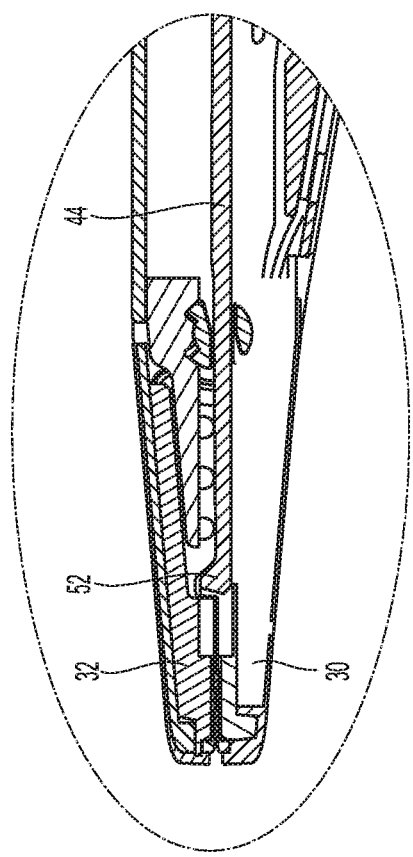
FIGS. 9-10 are enlarged cross-sectional views illustrating the knife shaft and the knife blade in the retracted and extended positions, respectively.
Figure 10:
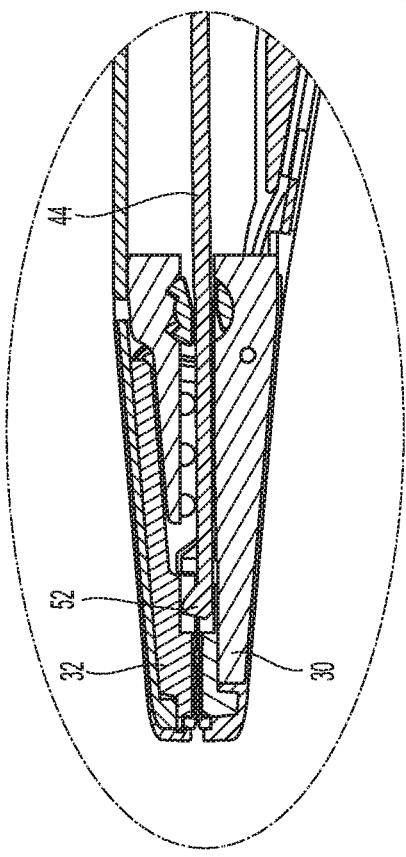

FIG. 9 illustrates the knife shaft 44 and the knife blade 52 in the retracted position and FIG. 10 illustrates the knife shaft 44 and the knife blade 52 in the extended position subsequent to actuation of the trigger 36. Upon achieving the extended position, the trigger 36 may be released causing the knife blade 52, the knife shaft 44 and the shaft plunger 50 to return to the retracted position of FIG. 4, i.e., a return stroke of the hydraulic knife mechanism, under the influence of the coil spring 54. During the return stroke, the shaft plunger 50 forces the fluid from the second receptacle section 38b to the first receptacle section 38a such that the trigger plunger 42 and the trigger 36 return to the initial position of FIG. 4 ready for subsequent actuation.

Although the hydraulic knife mechanism of the present disclosure is discussed in connection with its use in an electrosurgical forceps it is envisioned that the hydraulic knife mechanism may have application in many types of instruments involving linear movement of a component such as a knife blade. For example, the hydraulic knife mechanism may be incorporated into a conventional forceps instrument devoid of electrosurgical energy capabilities. Alternatively, the hydraulic knife mechanism could be modified to move any drive member associated with an instrument such as a staple pusher, clamping instrument or the like. Other uses are also envisioned.

The various embodiments disclosed herein may also be configured to work with robotic surgical systems and what is commonly referred to as "Telesurgery." Such systems employ various robotic elements to assist the surgeon and permit remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prepare the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto. No representation is made that the drawings are exactly to scale.

What is claimed is:

1. An electrosurgical forceps, comprising:
    a first member including a first housing and a first shaft member depending from the first housing, the first shaft member having a first jaw member with a tissue contacting surface;
    a second member including a second housing and a second shaft member depending from the second housing, the second shaft member having a second jaw member with a tissue contacting surface configured to communicate electrosurgical energy with the tissue contacting surface of the first jaw member, the second member configured for movement relative to the first member to cause movement of the first and second jaw members between open and closed positions;
    a fluid receptacle at least partially disposed within the first housing, the fluid receptacle defining first and second receptacle sections, the first receptacle section defining a first internal dimension and the second receptacle section defining a second internal dimension less than the first internal dimension;
    a fluid disposed within the fluid receptacle;
    a trigger plunger mounted within the first receptacle section and having a same diameter as the first receptacle section, the trigger plunger configured to push the fluid from the first receptacle section to the second receptacle section;
    a knife shaft at least partially disposed within the fluid receptacle distal of the trigger plunger and the fluid, and having a knife blade disposed adjacent the first and second jaw members;
    a manually engageable trigger mounted to the first housing and coupled to the trigger plunger, the trigger configured for linear movement a first linear distance to cause the trigger plunger to displace the fluid from the first receptacle section to the second receptacle section to cause corresponding linear movement of the knife shaft a second linear distance greater than the first linear distance whereby the knife blade at least partially traverses the first and second jaw members to sever tissue disposed therebetween.

2. The electrosurgical forceps according to claim 1 wherein the fluid disposed within the fluid receptacle is an incompressible fluid.

3. The electrosurgical forceps according to claim 1 wherein the knife shaft is configured to move from a retracted position to an extended position upon movement of the trigger the first linear distance.

4. The electrosurgical forceps according to claim 3 wherein the knife shaft includes a shaft plunger disposed within the second receptacle section of the fluid receptacle, the shaft plunger configured to be displaced by the fluid during movement of the trigger through the first linear distance to move the knife shaft to the extended position.

5. The electrosurgical forceps according to claim 4 wherein the knife shaft is normally biased toward the retracted position whereby upon release of the trigger subsequent to movement through the first linear distance, the knife shaft returns toward the retracted position with the shaft plunger displacing the fluid from the second receptacle section to the first receptacle section to cause the trigger plunger and the trigger to return to an initial position.

6. The electrosurgical forceps according to claim 1 wherein the fluid receptacle is a step design where the first receptacle section defines a first inner diameter and the second receptacle section defines a second inner diameter.

7. The electrosurgical forceps according to claim 6 wherein the ratio of the first inner diameter to the second inner diameter is greater than 1.5:1.

8. The electrosurgical forceps according to claim 7 wherein the ratio of the first inner diameter to the second inner diameter is at least 2:1.

9. A surgical forceps, comprising:
    a first member including a first housing and a first shaft member depending from the first housing, the first shaft member having a first jaw member;
    a second member including a second housing and a second shaft member depending from the second housing, the second shaft member having a second jaw member, the second member configured for movement relative to the first member to cause movement of the first and second jaw members between open and closed positions;

a fluid receptacle at least partially disposed within the first housing, the fluid receptacle defining first and second receptacle sections, the first receptacle section defining a first internal dimension and the second receptacle section defining a second internal dimension less the first internal dimension;

a trigger plunger mounted within the first receptacle section of the fluid receptacle and having a same diameter as the first receptacle section;

a knife shaft at least partially disposed within the second receptacle section, the knife shaft including a shaft plunger and a knife blade;

an incompressible fluid disposed within the fluid receptacle between the trigger plunger and the shaft plunger, the trigger plunger configured to push the incompressible fluid from the first receptacle section to the second receptacle section;

a manually engageable trigger mounted to the first housing and coupled to the trigger plunger, the trigger configured for linear movement through a first linear distance from an initial position to an actuated position to cause the trigger plunger to displace the incompressible fluid from the first receptacle section to the second receptacle section to cause corresponding engagement with the shaft plunger and linear movement of the knife shaft a second linear distance greater than the first linear distance whereby the knife blade at least partially traverses the first and second jaw members to sever tissue disposed therebetween.

10. The surgical forceps according to claim 9 wherein the knife shaft is normally biased to a retracted position whereby upon release of the trigger subsequent to movement to the actuated position, the shaft plunger engages the incompressible fluid to displace the incompressible fluid from the second receptacle section to the first receptacle section to cause linear movement of the plunger and return of the trigger to the initial position.

11. The surgical forceps according to claim 10 including a spring mounted in the first housing and engageable with the knife shaft to normally bias the knife shaft toward the retracted position.

12. The surgical forceps according to claim 9 wherein the fluid receptacle is a step design where the first receptacle section defines a first inner diameter and the second receptacle section defines a second inner diameter.

13. The surgical forceps according to claim 12 wherein the ratio of the first inner diameter to the second inner diameter is greater than 1.5:1.

14. The surgical forceps according to claim 13 wherein the ratio of the first inner diameter to the second inner diameter is at least 2:1.

15. The surgical forceps according to claim 9 wherein the first and second jaw members each include tissue contacting surfaces, the tissue contacting surfaces configured to communicate electrical energy therebetween.

16. The surgical forceps according to claim 15 including an electrosurgical generator in electrical communication with at least one of the first and second jaw members.

17. The electrosurgical forceps according to claim 1 wherein the trigger plunger is configured to contact a distal surface of the first receptacle section.

* * * * *